United States Patent
Shuster et al.

(10) Patent No.: US 6,816,250 B1
(45) Date of Patent: Nov. 9, 2004

(54) METHOD AND APPARATUS FOR MEASURING IRREGULARITIES ON AN OUTER SURFACE OF A ROTATABLE CYLINDRICAL SHAFT

(75) Inventors: Mark Shuster, Toledo, OH (US); Dana M. Combs, Maumee, OH (US); Donald K. Cohen, Farmington Hills, MI (US)

(73) Assignee: Dana Corporation, Toledo, OH (US)

( * ) Notice: Subject to any disclaimer, the term of this patent is extended or adjusted under 35 U.S.C. 154(b) by 163 days.

(21) Appl. No.: 09/879,866

(22) Filed: Jun. 12, 2001

Related U.S. Application Data

(60) Provisional application No. 60/210,748, filed on Jun. 12, 2000.

(51) Int. Cl.[7] .............................................. G01N 21/88
(52) U.S. Cl. .................................... 356/237.2; 356/600
(58) Field of Search ......................... 356/237.1, 237.2, 356/600, 601–613; 382/154, 141

(56) References Cited

U.S. PATENT DOCUMENTS

| | | | |
|---|---|---|---|
| 2,601,703 A | * | 7/1952 | Sawyer ..................... 264/40.1 |
| 3,907,438 A | | 9/1975 | Holeman |
| 4,102,578 A | | 7/1978 | Suzuki et al. |
| 4,764,016 A | | 8/1988 | Johansson |
| 4,806,777 A | | 2/1989 | Ulbers et al. |
| 5,355,221 A | | 10/1994 | Cohen et al. |
| 5,936,725 A | * | 8/1999 | Pike et al. ................ 356/237.1 |
| 6,160,910 A | * | 12/2000 | Freifeld ..................... 382/154 |
| 6,172,748 B1 | * | 1/2001 | Sones et al. ............. 356/237.1 |

OTHER PUBLICATIONS

A Quantitative Evaluation Of The Effects Of Shaft Lead And Hydrodynamic Flutes Upon Radial Lip Seal Performance, SAE Technical Paper Series No. 890995, dated Apr. 11–13, 1989.

\* cited by examiner

*Primary Examiner*—Richard A. Rosenberger
*Assistant Examiner*—Vincent P Barth
(74) *Attorney, Agent, or Firm*—MacMillan, Sobanski & Todd, LLC

(57) ABSTRACT

A method for measuring irregularities on the outer surface of an article employs an apparatus to obtain qualitative information regarding a first portion of the outer surface of the article, which can be used to generate a visual representation of a first portion of the outer surface of the article. Then, the article is moved by a predetermined amount, and the apparatus is again used to generate a visual representation of a second portion of the surface of the article. This process is repeated to obtain a plurality of visual representations that together span across a predetermined amount of the surface of the article. Then, the plurality of visual representations are processed to generate a single comprehensive enlarged visual representation of a relatively large surface area of the article, which is preferably shaded, colored, or otherwise highlighted to illustrate the irregularities that are formed therein. The single comprehensive enlarged visual representation can be used to analyze the nature of such irregularities.

10 Claims, 8 Drawing Sheets

METHOD AND APPARATUS FOR MEASURING IRREGULARITIES ON AN OUTER SURFACE OF A ROTATABLE CYLINDRICAL SHAFT

CROSS REFERENCE TO RELATED APPLICATION

This application claims the benefit of U.S. Provisional Application No. 60/210,748, filed Jun. 12, 2000, the disclosure of which is incorporated herein by reference.

BACKGROUND OF THE INVENTION

This invention relates in general to annular seals that resiliently engage the outer surfaces of cylindrical shafts to prevent passage of oil or other fluids therethrough when such shafts are rotated during use. In particular, this invention relates to an improved method and apparatus for measuring irregularities that are formed on the outer surface of a cylindrical shaft during manufacture so as to determine whether such irregularities would create a preferential lead when the shaft is rotated during use.

Annular seal assemblies are well known structures that are adapted to engage the outer surface of a rotatable shaft so as to prevent a fluid (such as oil) from passing therethrough when the shaft is rotated during use. One commonly known type of annular seal assembly is a radial lip seal assembly. A typical radial lip seal assembly includes a rigid outer annular case that is press fit within an opening formed through a housing of a machine or mechanism. An annular sealing element is secured to the case and extends radially inwardly into sealing engagement with an outer circumferential surface of a rotatable shaft. The radial lip seal assembly is designed to prevent the fluid from passing axially therethrough from one side thereof to the other side thereof as the shaft is rotated during use.

Traditionally, it has been believed to be desirable to form the outer circumferential surface of such a shaft to be perfectly smooth and concentrically located relative to the radial lip seal assembly. Such a perfectly smooth and concentrically oriented outer circumferential surface would allow for a smooth and uninterrupted engagement of the radially extending portion of the sealing element therewith so as to provide a fluid-tight engagement. However, as a practical matter, the outer circumferential surface of the shaft is never perfectly smooth, but rather has a variety of irregularities formed therein during manufacture. Furthermore, at least in some instances, the presence of some of such irregularities has been found to be desirable because they provide small recesses that can retain fluid therein. Such fluid can function as a lubricant to minimize the adverse effects of friction and heat that would otherwise be generated at the sealing element when the shaft is rotated during use.

It has been found that if the irregularities are relatively small in size and sufficiently randomly distributed over the outer circumferential surface of the shaft, then their presence will not likely affect the operation of the radial lip seal assembly. However, if such irregularities are relatively large or are not sufficiently randomly distributed over the outer circumferential surface of the shaft, then their presence may advantageously or adversely affect the operation of the radial lip seal assembly. Such an affect can occur when the irregularities are sized and oriented in such a manner as to function in the manner of a helical thread formed in the outer circumferential surface of the shaft, referred to herein as a preferential lead. It is known that such a helical thread or preferential lead, when oriented in the correct direction, can advantageously function with the sealing element to resist fluid leaking therethrough by essentially pumping it back to the fluid side of the radial lip seal assembly. It is also known, however, that such a helical thread or preferential lead, when oriented in the incorrect direction, can adversely function against the sealing element to promote fluid leakage by pumping it through to the air side of the radial lip seal assembly. Thus, to insure that the radial lip seal assembly functions satisfactorily, it has been found to be important to determine whether the outer circumferential surface of the shaft possesses a preferential lead and, if so, in which direction such preferential lead is oriented.

Unfortunately, the size and orientation of the irregularities formed in the outer circumferential surface of the shaft are so small as to be not visible to the naked eye or otherwise readily ascertainable. The traditional method of determining the magnitude and direction of the preferential lead is to hang a pair of weights on opposite sides of the shaft by means of a thin thread, and then rotate the shaft. If a preferential lead is present on the shaft, the thread and the weights will be move in an axial direction along the shaft. The direction and speed of such movement is indicative of the magnitude and direction of the preferential lead. Although effective, this method has been found to be time consuming and imprecise. Accordingly, it would be desirable to provide an improved method and apparatus for measuring the irregularities on the outer circumferential surface of a cylindrical shaft to determine whether such irregularities create a preferential lead when the shaft is rotated during use and, if so, in which direction such preferential lead is oriented.

SUMMARY OF THE INVENTION

This invention relates to an improved method and apparatus for measuring the irregularities on the outer circumferential surface of a cylindrical shaft to determine whether such irregularities create a preferential lead when the shaft is rotated during use. An apparatus, such as an interferometric measuring device, is used to obtain qualitative information regarding a first portion of the outer circumferential surface of the shaft. That qualitative information can be used to generate a two dimensional or three dimensional visual representation of a first portion of the outer circumferential surface of the shaft. Then, the shaft is rotated by a predetermined amount, and the apparatus is again used to generate a visual representation of a second portion of the outer circumferential surface of the shaft. This process is repeated as necessary to obtain a plurality of visual representations that together span across a predetermined amount, fifteen degrees, for example, of the outer circumferential surface of the shaft. The size of this circumferential span may be selected as desired. Following this acquisition, the plurality of visual representations are processed by an image processor so as to generate a single comprehensive enlarged visual representation of a relatively large surface area of the outer circumferential surface of the shaft. The enlarged visual representation is preferably shaded, colored, or otherwise highlighted to illustrate the irregularities that are formed in the relatively large surface area of the outer circumferential surface of the shaft. The single comprehensive enlarged visual representation can be analyzed to determine whether such irregularities create a preferential lead when the shaft is rotated during use and, if so, in which direction such preferential lead is oriented.

Various objects and advantages of this invention will become apparent to those skilled in the art from the following detailed description of the preferred embodiments, when read in light of the accompanying drawings.

DETAILED DESCRIPTION OF THE PREFERRED EMBODIMENTS

Figure 1:
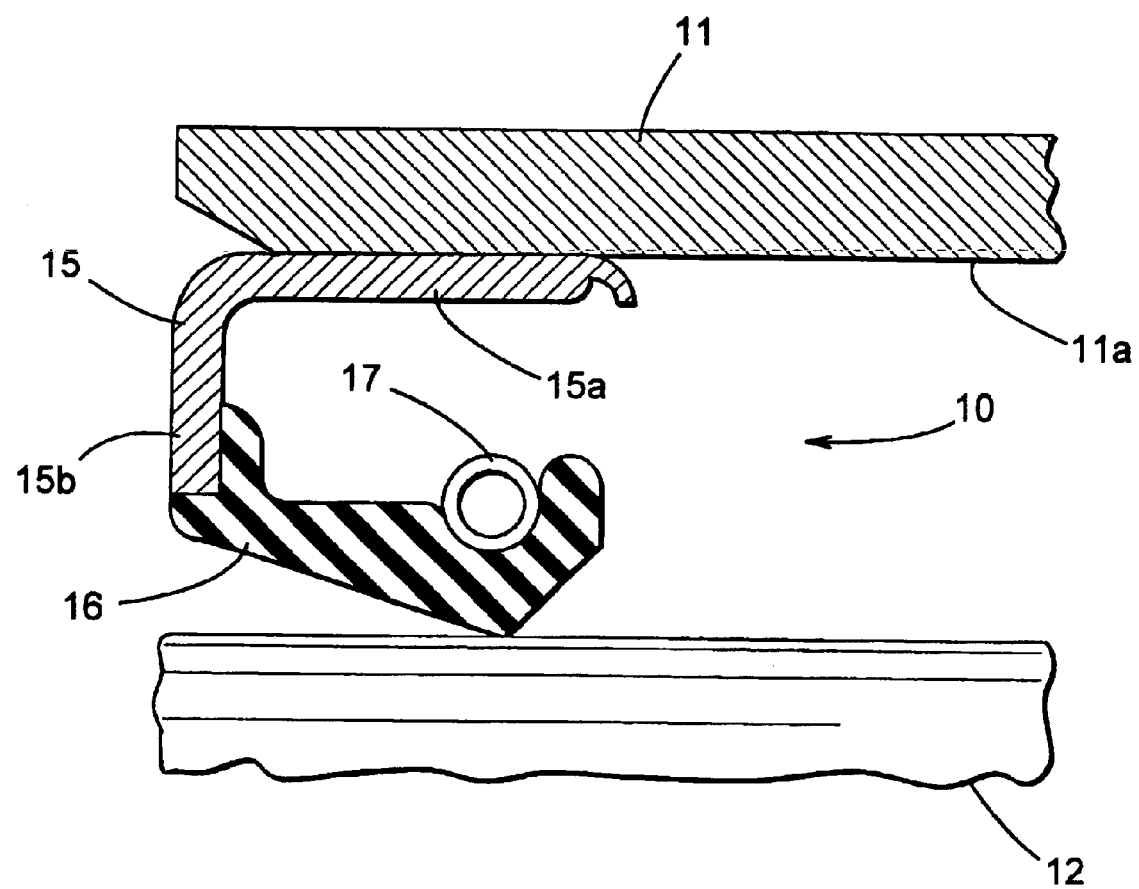
FIG. 1 is a sectional elevational view of a portion of a conventional radial lip seal assembly disposed within an opening formed through a housing and about a rotatable cylindrical shaft.

Referring now to the drawings, there is illustrated in FIG. 1 a conventional structure for a radial lip seal assembly, indicated generally at 10, for providing a seal between a housing 11 and a rotatable shaft 12. The housing 11 is intended to be representative of any machine or mechanism having an opening 11a through which at least a portion of the shaft 12 extends and is rotated relative thereto during use. The radial lip seal assembly 10 includes an outer annular case 15 that is typically formed from a metallic or otherwise rigid material. In the illustrated embodiment, the case 15 is generally L-shaped in cross section, having an axially extending portion 15a and a radially extending portion 15b. However, the case 15 may be formed having any desired shape or configuration. The outer diameter defined by the axially extending portion 15a of the case 15 is usually sized to be slightly larger that the inner diameter defined by the opening 11a such that the case 15 can be installed within the opening 11a formed through the housing 11 in a press fit relationship. The radially extending portion 15b of the case 15 extends radially inwardly and terminates at a location that is spaced apart from the outer circumferential surface of the shaft 12.

The radial lip seal assembly 10 also includes an annular sealing element 16 that is usually secured to the radially extending portion 15b of the case 15, such as by an adhesive. The sealing element 16 is typically formed from a flexible material, such as an elastomeric material, and includes a portion that extends radially inwardly into engagement with the outer circumferential surface of the shaft 12. If desired, an annular garter spring 17 or other biasing mechanism can be provided to positively urge the portion of the sealing element 16 radially inwardly into engagement with the outer circumferential surface of the shaft 12.

The radial lip seal assembly 10 is designed to prevent a fluid (such as oil) from passing axially therethrough from one side thereof (typically the right side when viewing FIG. 1) to the other side thereof (typically the left side when viewing FIG. 1) as the shaft 12 is rotated during use. To accomplish this, the radially inwardly extending portion of the sealing element 16 engages the outer circumferential surface of the shaft 12. As discussed above, the outer circumferential surface of the shaft 12 is not perfectly smooth, but rather has a variety of irregularities formed therein. Such irregularities can, when the shaft 12 is rotated, function to provide a preferential lead that can either advantageously or adversely affect the performance of the radial lip seal assembly 10, depending upon orientation of the shaft 12 relative to the radial lip seal assembly 10.

Figure 2:
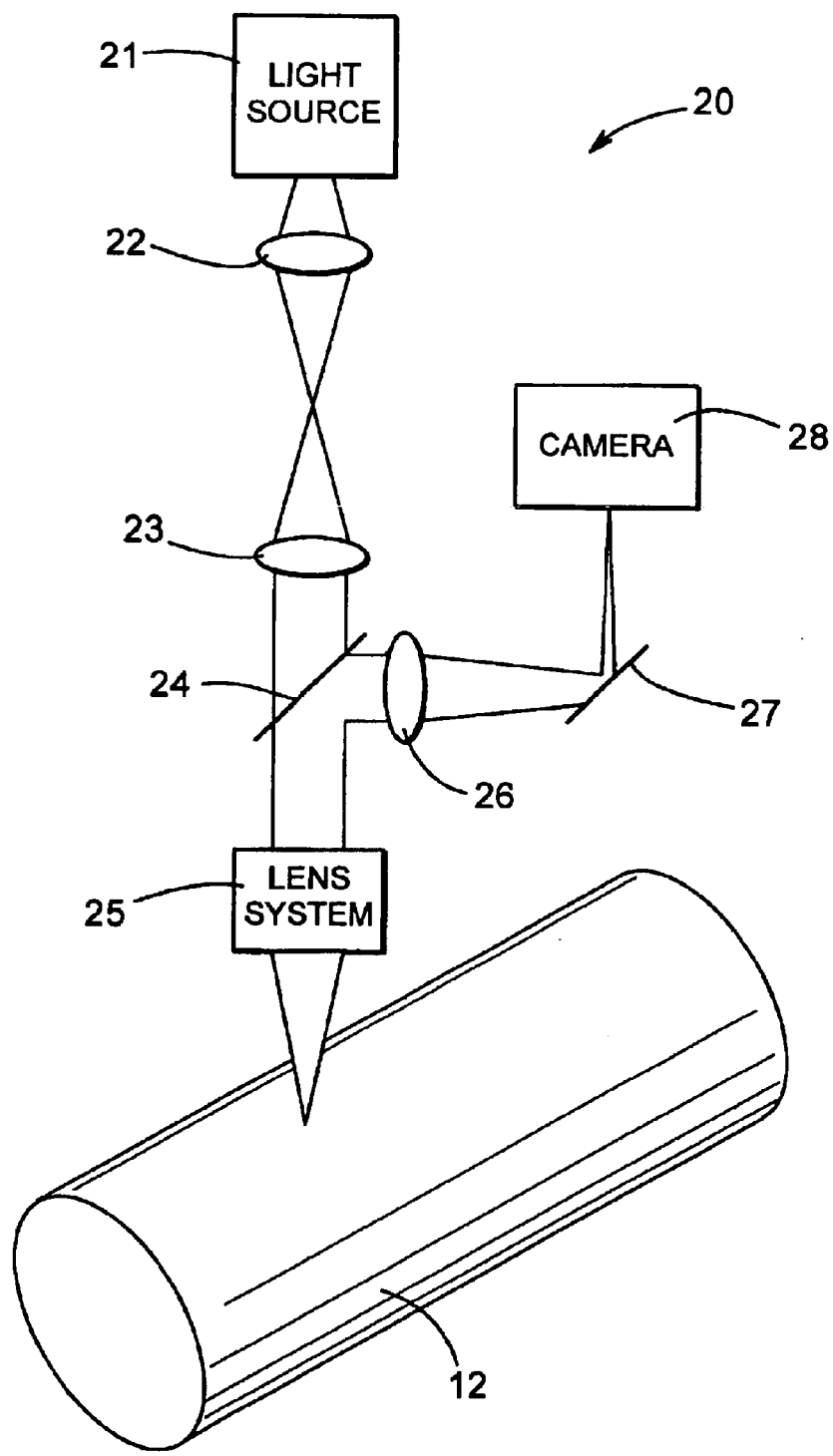
FIG. 2 is a schematic diagram of a first embodiment of an apparatus for generating an enlarged visual representation of a single relatively small area of the outer circumferential surface of the shaft illustrated in FIG. 1.

FIG. 2 schematically illustrates the structure of a first embodiment of an apparatus, indicated generally at 20, for generating an enlarged visual representation of a single relatively small area of the outer circumferential surface of the shaft 12 illustrated in FIG. 1. In the illustrated embodiment, the apparatus 20 is an interferometric measuring device that is designed to generate a quantitative analysis (i.e., a mathematical representation) of the single relatively small area of the outer circumferential surface of the shaft 12. Such an interferometric measuring device is disclosed in U.S. Pat. No. 5,355,221 to Cohen et al., the disclosure of which is incorporated herein by reference. Briefly, however, such apparatus 20 includes a light source 21 that generates a beam of light through a pair of aligning lens 22 and 23, a beam splitter 24, and an interferometric lens system 25 onto a relatively small area of the outer circumferential surface of the shaft 12. The beam of light is reflected from the illuminated relatively small area of the outer circumferential surface of the shaft 12 back to the beam splitter 24, where it is reflected through a lens 26 and a mirror 27 into a camera 28. The camera 28 generates a mathematical representation of the illuminated portion of the outer circumferential surface of the shaft 12 which can be used to generate a visual representation thereof, typically in digital signal form.

The structure and operation of the apparatus 20 is conventional in the art and, therefore, requires no detailed explanation. Although this invention will be described in the context of the illustrated apparatus 20, it will be appreciated that this invention may be practiced using any device that is capable of generating a quantitative analysis and/or an enlarged visual representation of a portion of the outer circumferential surface of the shaft 12. A variety of interference microscopes and similar optical profilers are available from the Wyko Optical Profilers Group of Veeco Instruments Inc. in Tucson, Ariz.

Figure 3:
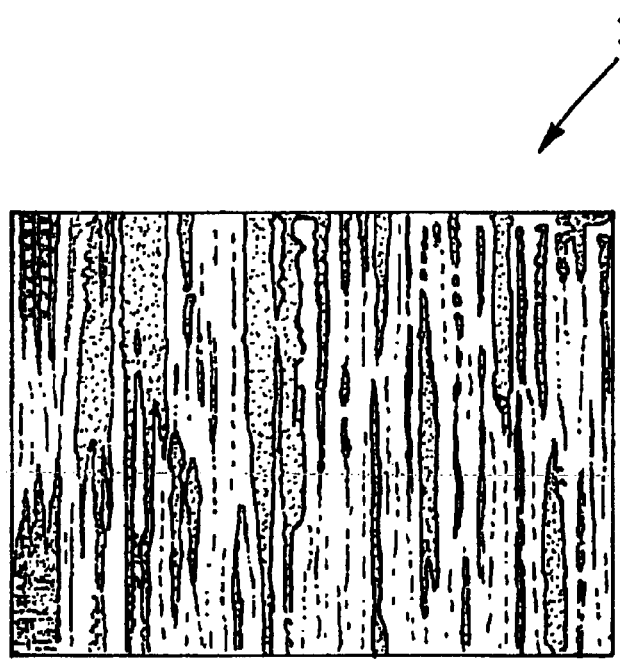
FIG. 3 is an enlarged two dimensional visual representation generated by the apparatus illustrated in FIG. 1 of the single relatively small area of the outer circumferential surface of the shaft illustrated in FIG. 1.
Figure 4:
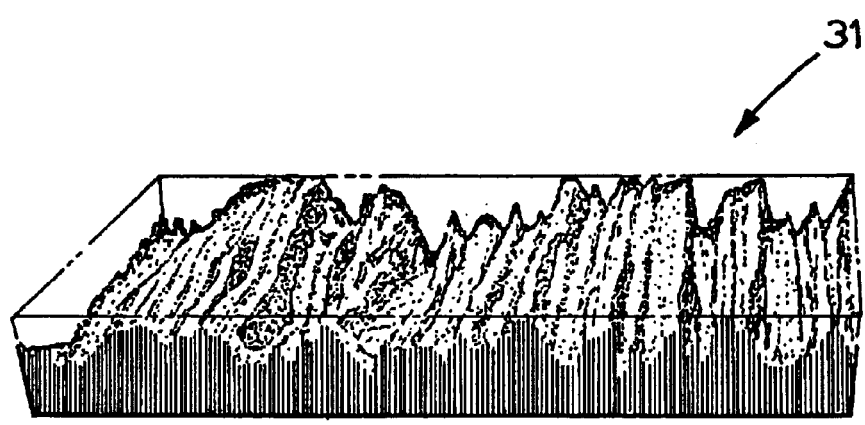
FIG. 4 is an enlarged three dimensional visual representation generated by the apparatus illustrated in FIG. 1 of the single relatively small area of the outer circumferential surface of the shaft illustrated in FIG. 1.

The visual representation generated by the camera 28 can be stored in a conventional electronic controller (not shown)

and processed for visual display, such as on a video terminal or in hard copy form. Samples of the enlarged visual representations that can be generated by the apparatus 20 are illustrated in FIGS. 3 and 4. FIG. 3 is a two dimensional visual representation, indicated generally at 30, while FIG. 4 is a three dimensional visual representation, indicated generally at 31. As shown therein, the enlarged visual representations 30 and 31 are preferably shaded, colored, or otherwise highlighted to illustrate the irregularities that are formed in the outer circumferential surface of the shaft 12. For example, such irregularities can be characterized as small peaks and valleys relative to the nominal outer diameter of the shaft 12. Thus, such peaks and valleys can be characterized as having heights that differ relative to the nominal outer diameter of the shaft 12. The magnitude of these different heights (which were obtained using the above-mentioned quantitative analysis) can be represented by differing shades of gray, differing colors, or any other desired designation in the enlarged visual representations 30 and 31.

Analysis of the enlarged visual representations 30 and 31 is then performed to determine whether the illustrated irregularities create a preferential lead when the shaft 12 is rotated during use and, if so, in which direction such preferential lead is oriented. Such analysis may be performed manually by an operator merely by viewing such enlarged visual representations 30 and 31. Alternatively, such analysis may be performed semi-automatically or fully automatically by an electronic computing apparatus that has been programmed with a predetermined algorithm. The analysis may be quantitative in nature (such as based upon the mathematical representations described above) or qualitative in nature (such as based upon the visual representations described above). Such computer hardware and software is commercially available from the Wyko Optical Profilers Group of Veeco Instruments Inc. in Tucson, Ariz.

Although the enlarged visual representations 30 and 31 do illustrate the irregularities formed in the outer circumferential surface of the shaft 12, the physical size of the illustrated surface area is, in both instances, relatively small. Typically, the physical size of the surface area illustrated in the enlarged visual representations 30 and 31 is only approximately 0.04 inch by approximately 0.04 inch. In some instances, it may be possible to detect the presence of a preferential lead in the outer circumferential surface of the shaft 12 from the relatively small visual representations 30 and 31. However, more often, the physical size of the surface area illustrated in the enlarged visual representations 30 and 31 is too small to accurately determine whether the outer circumferential surface of the shaft 12 possesses a preferential lead and, if so, in which direction such preferential lead is oriented.

Figure 5:
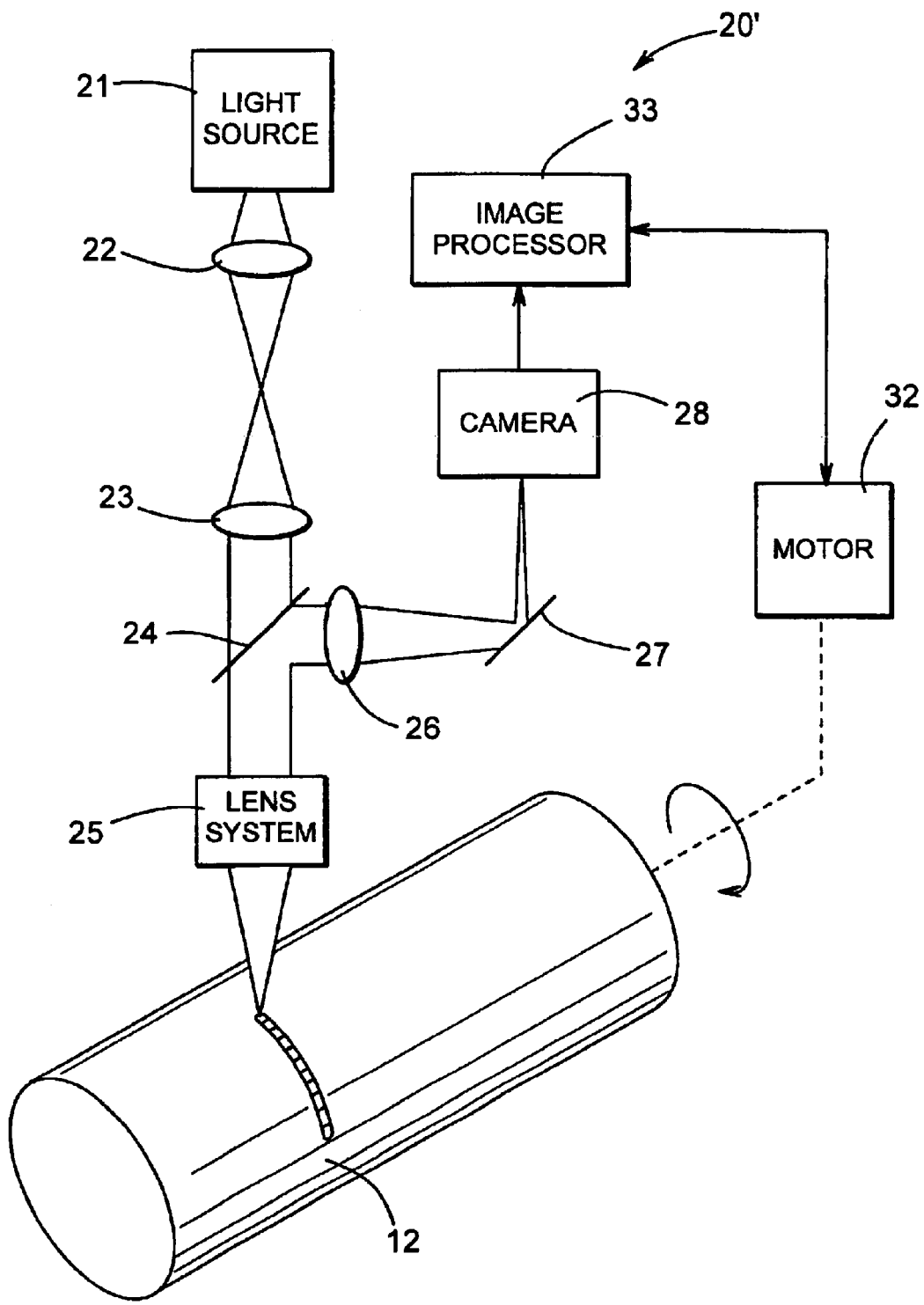
FIG. 5 is a schematic diagram of a second embodiment of an apparatus for generating an enlarged visual representation of a comprehensive relatively large area of the outer circumferential surface of the shaft illustrated in FIG. 1.

To address this, this invention contemplates that a plurality of such enlarged visual representations 30 and 31 be generated to illustrate the irregularities that are formed in a relatively large surface area of the outer circumferential surface of the shaft 12. To accomplish this, a second embodiment of an apparatus, such as indicated generally at 20' in FIG. 5, can be used. The components of the illustrated apparatus 20' are, in large measure, the same as the components of the apparatus 20 illustrated FIG. 2, and like reference numbers are used to illustrate similar components. However, the apparatus 20' further includes a precision motor 32 or other mechanism for selectively re-positioning the shaft 12 in the manner described in further detail below relative to the remainder of the apparatus 20'. The apparatus 20' also includes an image processor 33 that receives signals from the camera 28 to generate enhanced visual representations in the manner also described in further detail below.

As mentioned above, the camera 28 generates a visual representation, typically in digital signal form, of the illuminated area of the outer circumferential surface of the shaft 12. Once a first visual representation of a first illuminated area of the shaft 12 has been acquired by the image processor 33, the motor 32 is energized to rotate or otherwise move the shaft 12 by a predetermined amount. The motor 32 can be energized manually by an operator. Alternatively, as shown by the connection between the motor 32 and the image processor 33, the motor 32 can be energized automatically to rotate or otherwise move the shaft when the image processor 33 has completed its acquisition of the current visual representation. Preferably, the shaft 12 is rotated relative to the apparatus 20' with little or no axial movement of the shaft 12. The amount of such rotation is preferably dependent upon the physical size of the image acquired by the image processor. Preferably, the shaft 12 is rotated by such an amount that the beam of light from the light source 21 is focused on a second illuminated area of the outer circumferential surface of the shaft 12 adjacent to the first illuminated area. For reasons that will be explained below, it may be desirable for the second illuminated area to overlap a relatively small portion of the first illuminated area. Once the shaft 12 has been properly re-positioned in this manner, a second visual representation of the second illuminated area of the shaft 12 is acquired by the image processor 33. This process is repeated as necessary to obtain a plurality of visual representations that, together as a group, span across a predetermined amount of the outer circumferential surface of the shaft 12.

Figures 6, 7:
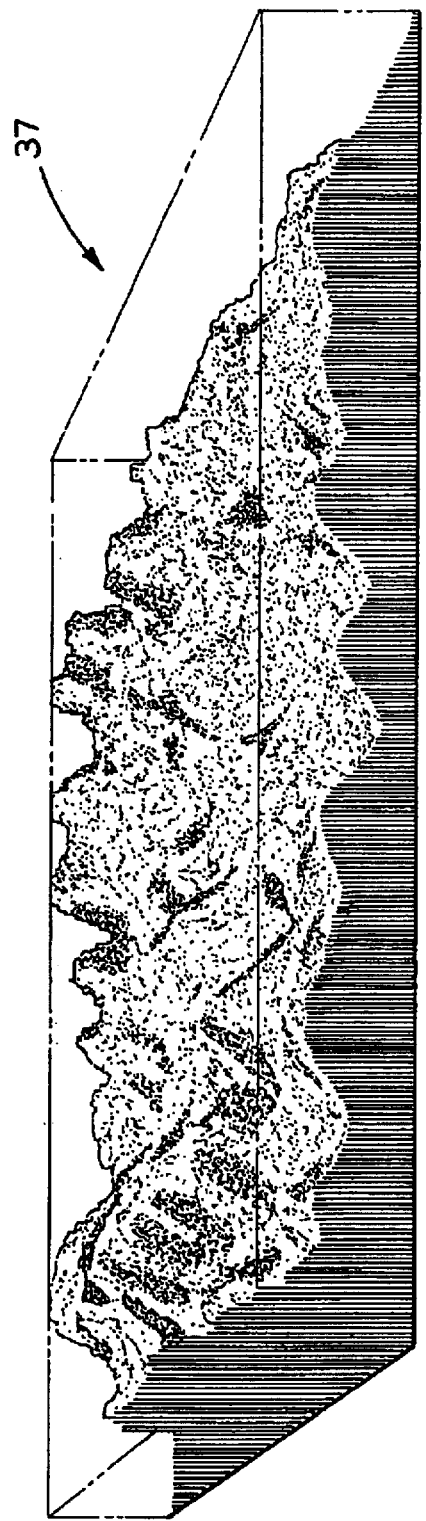
FIG. 6 is an enlarged two dimensional visual representation generated by the apparatus illustrated in FIG. 5 of the single comprehensive enlarged visual representation of a relatively large surface area of the outer circumferential surface of the shaft illustrated in FIG. 1.
FIG. 7 is an enlarged three dimensional visual representation generated by the apparatus illustrated in FIG. 5 of the single comprehensive enlarged visual representation of a relatively large surface area of the outer circumferential surface of the shaft illustrated in FIG. 1.

Following each acquisition, the visual representations generated by the camera 28 can be stored in a conventional electronic controller (not shown). Then, the plurality of visual representations are processed by the image processor 33 so as to generate a single comprehensive enlarged visual representation of a relatively large surface area of the outer circumferential surface of the shaft 12. Samples of the comprehensive enlarged visual representation that can be generated by the apparatus 20' are illustrated in FIGS. 6 and 7. FIG. 6 is a two dimensional visual representation, indicated generally at 36, while FIG. 7 is a three dimensional visual representation, indicated generally at 37. As shown therein, the enlarged visual representations 36 and 37 are preferably shaded, colored, or otherwise highlighted to illustrate the irregularities that are formed in the relatively large surface area of the outer circumferential surface of the shaft 12. As described above, such irregularities can be characterized as small peaks and valleys relative to the nominal outer diameter of the shaft 12. Thus, such peaks and valleys can be characterized as having heights that differ relative to the nominal outer diameter of the shaft 12. The magnitude of these different heights can be represented by differing shades of gray, differing colors, or any other desired designation in the enlarged visual representations 36 and 37.

The processing of the plurality of visual representations to generate the single comprehensive enlarged visual representation of a relatively large surface area of the outer circumferential surface of the shaft 12 can be accomplished using known image processing techniques. Preferably, the image processor 33 includes an electronic controller that is programmed to accomplish this task. Such hardware and software is commercially available from the Wyko Optical Profilers Group of Veeco Instruments Inc. in Tucson, Ariz. As mentioned above, it has been found to be desirable that the sequentially acquired illuminated areas to overlap one another by at least a relatively small portion. Such overlapping facilitates the processing of the plurality of visual representations to generate the single comprehensive enlarged visual representation of a relatively large surface area of the outer circumferential surface of the shaft 12.

As mentioned above, the acquisition process is repeated as necessary to obtain a plurality of visual representations that together span across a predetermined amount of the outer circumferential surface of the shaft 12. The size of this circumferential span may be selected as desired to insure that a sufficient amount of the outer circumferential surface of the shaft 12 is sampled to enable a determination of the magnitude and orientation of the preferential lead (if any) formed therein. The size of this measurement will depend, among other things, on the angle measured in each acquisition and the radius of the shaft 12. For example, a circumferential span of approximately fifteen degrees has been found to function satisfactorily.

The axial width of each measurement may also be varied as desired. It has been found to be desirable for each measurement to be at least 0.04 inch in axial width. If desired, the acquisition process can be performed to acquire visual representations in the axial direction, either in combination with or in lieu of the visual representations in the circumferential direction.

The relatively small visual representations 30 and 31 and the comprehensive visual representations 36 and 37 illustrate a combination of both relatively large irregularities and relatively small irregularities that are formed in the outer circumferential surface of the shaft 12. The relatively large irregularities have been found to be the result of preliminary machining operations, such as turning, performed on the shaft 12 at or near the beginning of the manufacturing process. Such relatively large irregularities have been found to make a large contribution toward the presence of a preferential lead on the shaft 12. The relatively small irregularities, on the other hand, have been found be the result of subsequent finishing operations, such as grinding, performed on the shaft 12 at or near the conclusion of the manufacturing process. Such relatively small irregularities have been found to make a small contribution, if any, toward the presence of a preferential lead on the shaft 12.

Thus, to facilitate the analysis of the relatively small visual representations 30 and 31 and the comprehensive visual representations 36 and 37, it may be desirable to employ a digital low pass filter (not shown) to remove the shorter wavelength features from the relatively small visual representations 30 and 31 and the comprehensive visual representations 36 and 37. Such a digital low pass filter is conventional in the art and is designed to remove shorter wavelength features that do not contribute, at least significantly, toward the presence of a preferential lead on the shaft 12. By removing such shorter wavelength features from the relatively small visual representations 30 and 31 and the comprehensive visual representations 36 and 37, the analysis of the remaining larger wavelength features is facilitated.

The shaft 12 is typically manufactured by performing a series of metal working processing steps on a blank of raw metal stock. For example, a blank of raw metal stock may be subjected to a rough turning process, a finish turning process, a quenching process, and a finish plunge grinding process to form the final shaft 12. It will be appreciated that these four processing steps are intended to be representative of any desired number or type of metal working or other processes that can be performed on the shaft 12. It will further be appreciated that each of these processes can create irregularities in the outer circumferential surface of the shaft 12. To improve the overall manufacturing process, a visual representation can be made of a portion of the outer circumferential surface of the shaft 12 after the performance of some or all of the processing steps. By analyzing such visual representations, a determination be made as to whether a preferential lead is present on the outer circumferential surface of the shaft 12 and, if so, what the orientation of such preferential lead is. Additionally, however, by comparing such visual representations, an analysis can be made of the overall manufacturing process. Specifically, it can be determined at which point in the manufacturing process that the preferential lead is being generated and, in some instances, how to prevent or minimize the size thereof.

Figures 8, 9, 10, 11:
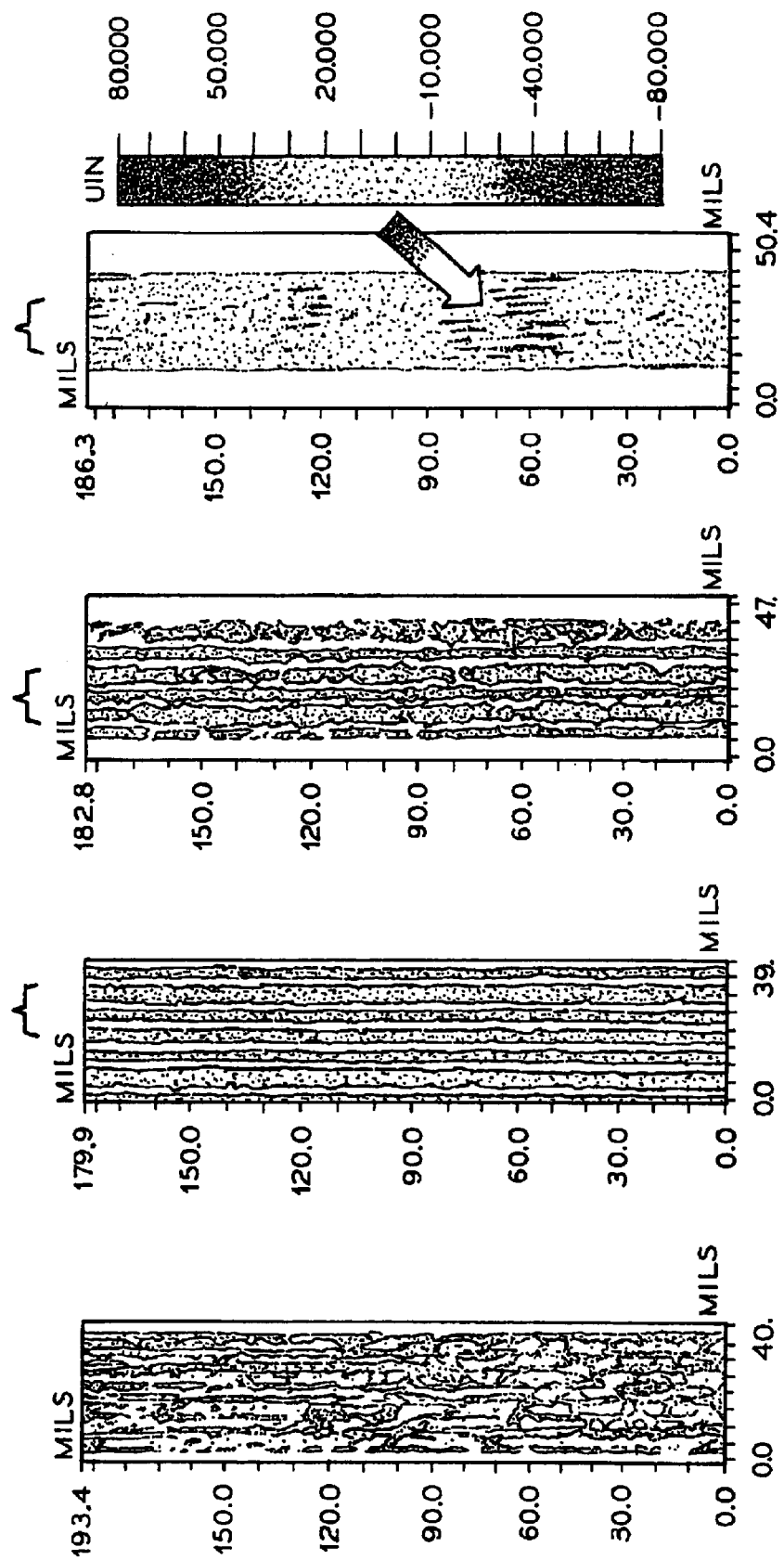
FIG. 8 is a comprehensive visual representation of the shaft illustrated in FIG. 1 after being subjected to a first rough turning process.
FIG. 9 is a comprehensive visual representation of the shaft illustrated in FIG. 1 after being subjected to a second finish turning process.
FIG. 10 is a comprehensive visual representation of the shaft illustrated in FIG. 1 after being subjected to a third quenching process.
FIG. 11 is a comprehensive visual representation of the shaft illustrated in FIG. 1 after being subjected to a fourth finish plunge grinding process.

FIGS. 8 through 11 illustrate comprehensive visual representations of the outer surface of the shaft 12 at the conclusion of four processing steps in the manufacture thereof. FIG. 8 is a comprehensive visual representation of the shaft 12 after being subjected to a first rough turning process. FIG. 9 is a comprehensive visual representation of the shaft 12 after being subjected to a second finish turning process. FIG. 10 is a comprehensive visual representation of the shaft 12 after being subjected to a third quenching process. FIG. 11 is a comprehensive visual representation of the shaft 12 after being subjected to a fourth finish plunge grinding process. As shown by the bracketed portions in FIGS. 9, 10, 11, the preferential lead formed in the outer circumferential surface of the illustrated shaft 12 after being subjected to the second finish turning process possesses the same lead angle and lateral distance between adjacent lowered areas as it does after the fourth plunge grinding process. This similarity indicates that an insufficient allowance for grind lock was made in the fourth finish plunge grinding process. Furthermore, the portion of the comprehensive visual representation of the shaft 12 after being subjected to a fourth finish plunge grinding process highlighted by the arrow in FIG. 11 represents a recessed area on the shaft 12 that could result in chattering on the surface of the shaft 12 during use. Thus, it can be seen that an analysis of the visual representations made at differing points of the manufacture of the shaft 12 can allow a determination be made as to whether the overall manufacturing process is satisfactory or should be changed to enhance the quality of the outer circumferential surface of the final shaft 12.

The invention has been described in the context of the cylindrical, rotatable shaft 12 that is adapted for use with the seal assembly 10 illustrated in FIG. 1 to determine the presence and orientation of a preferential lead. However, it will be appreciated that this invention may be used to generate a visual representation of any desired surface of any desired article for any desired purpose. For example, either the apparatus 20 or the apparatus 20' described above may be used to generate visual representations of the surfaces of a gear to analyze and reduce the effects of wear thereon during use.

Figure 12:
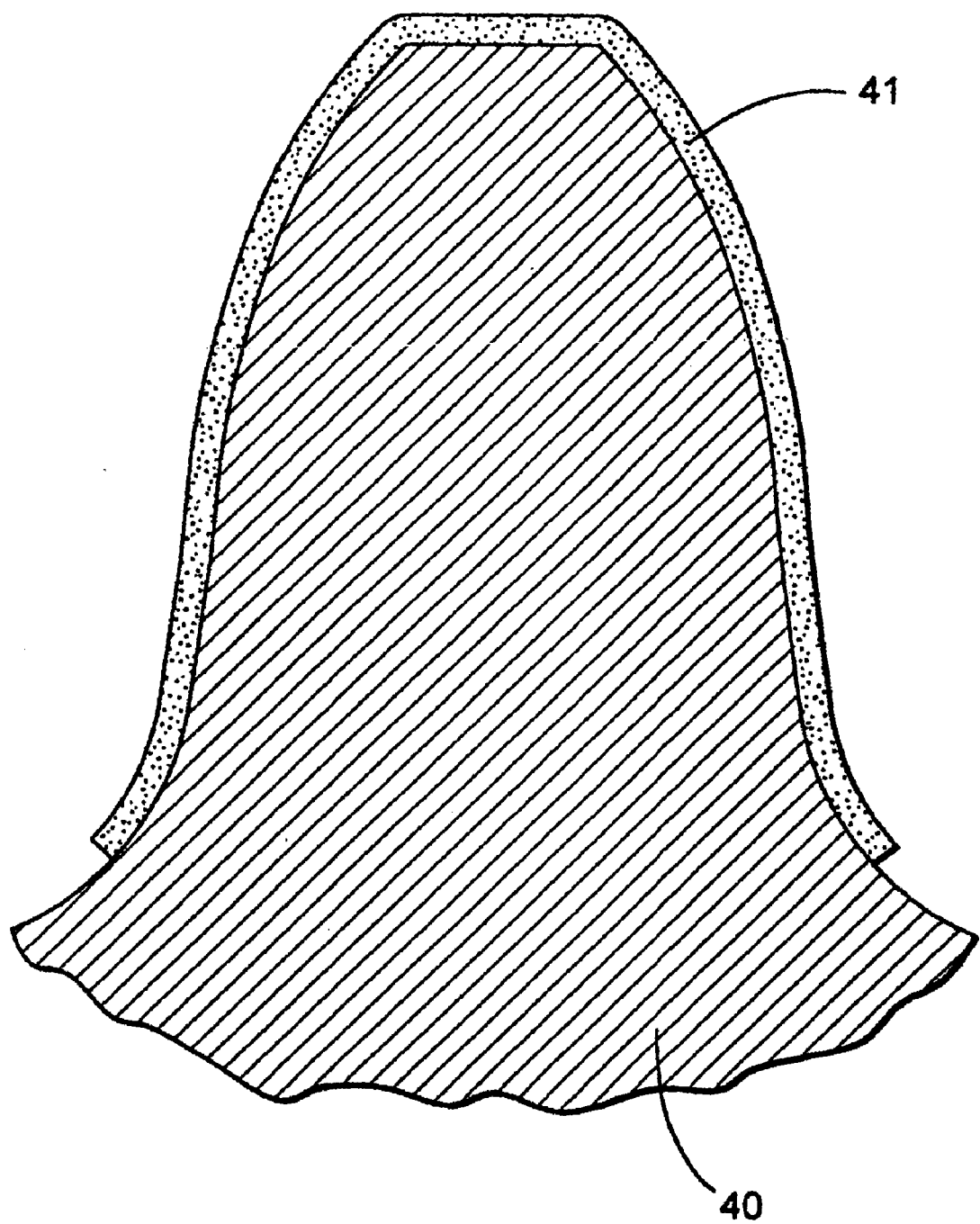
FIG. 12 is an enlarged sectional elevational view of a tooth of a gear having a layer of a film applied thereto.

FIG. 12 is an enlarged sectional elevational view of a tooth 40 of a conventional gear. The tooth 40 is intended to be representative of any mechanical structure having a surface that is desired to be analyzed in the manner described above. In the illustrated embodiment, it will be appreciated that the configuration of the outer surface of the tooth 40 of the gear is quite irregular in shape in comparison to the cylindrical shaft 12 discussed above. In instances such as this, the use of the apparatus 20 or 20' may be somewhat awkward because of the non-flat or circular shape of the outer surface of the article to be illuminated and analyzed.

Figure 13:
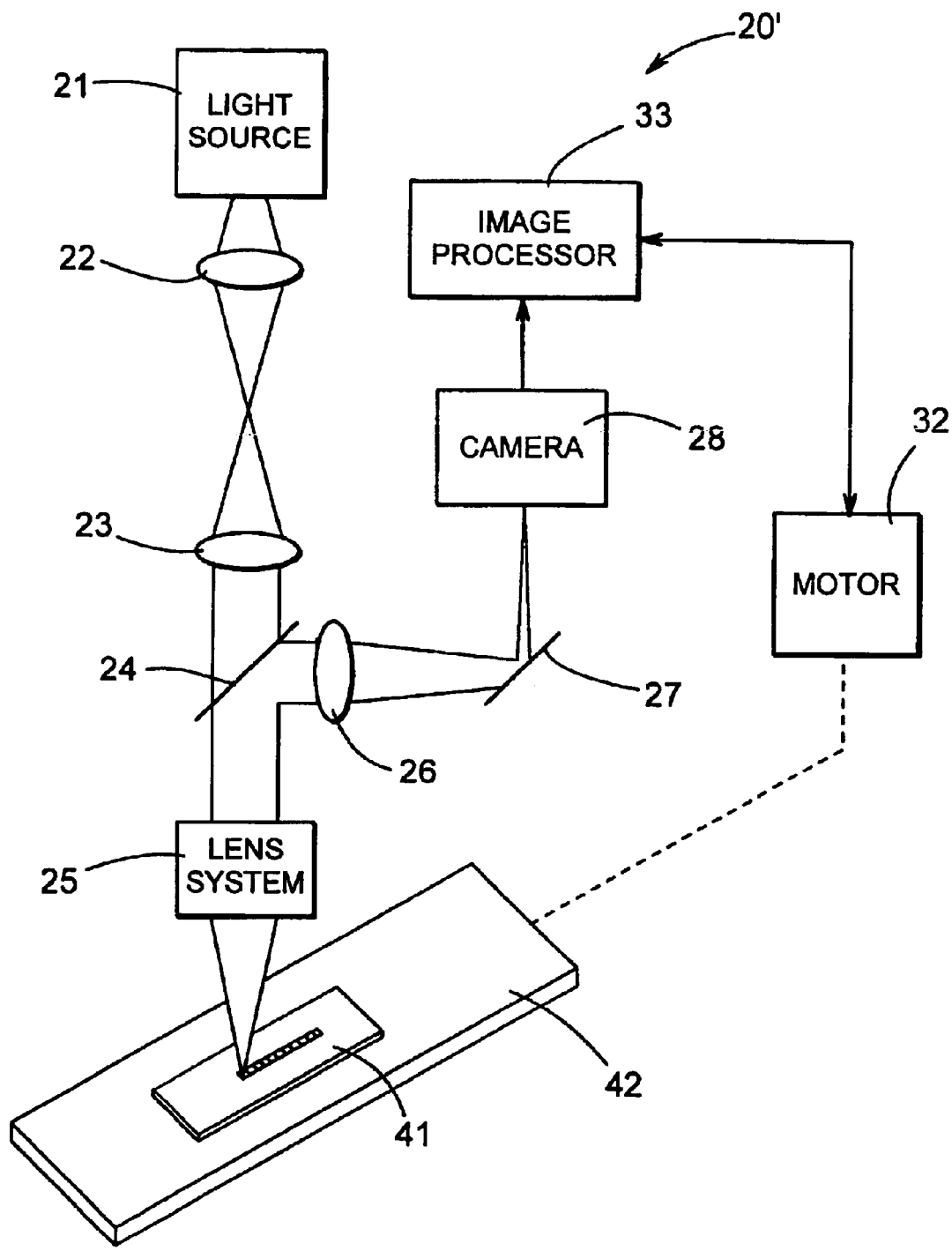
FIG. 13 is a schematic diagram of the apparatus illustrated in FIG. 5 for generating an enlarged visual representation of a comprehensive relatively large area of the outer surface of the gear illustrated in FIG. 12.

In order to facilitate the use of the apparatus 20 or 20', a film 41 is applied to or otherwise contacted with the portion or portions of the outer surface of the tooth 40 to be illuminated and analyzed. Such film 41 is preferably formed from a material that is somewhat flexible so that when it is applied to the outer surface of the tooth 40 of the gear, it conforms its shape to the shape of the outer surface of such tooth 40. Thus, when it is applied to such outer surface, the film 41 is deformed to acquire the same surface characteristics as the portion of the outer surface of the tooth 40 of the gear to be illuminated and analyzed. Then, the film 41 is removed from the tooth 40 of the gear and laid flat, such as on a support surface 42 shown in FIG. 13 if desired.

Thereafter, the apparatus 20 or 20' may be used in the manner described above to generate one or more visual representations of the deformed portions thereof. The analysis of such visual representations can be made in the manner described above to provide a determination of the outer surface of the tooth 40 of the gear.

It will be appreciated that the film 41 is intended to be representative of any desired material that can be used to acquire a replica having the same surface characteristics as the portion of the outer surface of the tooth 40 of the gear to be illuminated and analyzed, which replica can subsequently be re-shaped to facilitate the use of the apparatus 20 or 20'. For example, the replicating media may include putty and clay materials, elastomeric materials, silicone based resins, and similar materials that are sufficiently dimensionally stable to form a solid impression of the portion of the outer surface of the tooth 40 of the gear to be illuminated and analyzed.

In accordance with the provisions of the patent statutes, the principle and mode of operation of this invention have been explained and illustrated in its preferred embodiment. However, it must be understood that this invention may be practiced otherwise than as specifically explained and illustrated without departing from its spirit or scope.

What is claimed is:

1. A method for analyzing irregularities formed in a surface of a rotatable article to determine the presence of a preferential lead comprising the steps of:
   (a) obtaining a plurality of representations of different, relatively small areas of the irregularities formed in the surface of the article;
   (b) processing the plurality of representations to generate a single representation of a relatively large area of the irregularities formed in the surface of the article; and
   (c) analyzing the single representation of the relatively large area of the irregularities formed in the surface of the article to determine the presence of a preferential lead.

2. The method defined in claim 1 wherein said step (a) is performed by obtaining qualitative information regarding the plurality of different, relatively small areas of the surface of the article.

3. The method defined in claim 2 wherein said step (a) is further performed by obtaining a mathematical representation of the plurality of different, relatively small areas of the surface of the article.

4. The method defined in claim 2 wherein said step (a) is further performed by using the quantitative information to generate a visual representation of each of the plurality of different, relatively small areas of the surface of the article.

5. The method defined in claim 4 wherein said visual representations are two dimensional.

6. The method defined in claim 4 wherein said visual representations are three dimensional.

7. The method defined in claim 1 wherein said step (a) is performed by contacting a material with the surface of the article so that a surface of the material acquires the same characteristics as the surface of the article, and obtaining a plurality of representations of different, relatively small areas of the surface of the material.

8. The method defined in claim 7 wherein the material is a film that is applied to the article.

9. The method defined in claim 1 wherein the article is generally cylindrical in shape, and wherein said step (a) is performed by obtaining a plurality of representations of different, relatively small areas extending circumferentially about the surface of the article.

10. The method defined in claim 1 wherein said step (c) is performed by an electronic computing apparatus that has been programmed with a predetermined algorithm.

* * * * *